United States Patent
Maurer et al.

(10) Patent No.: US 12,396,998 B2
(45) Date of Patent: *Aug. 26, 2025

(54) TREATMENT FOR HEART FAILURE WITH PRESERVED EJECTION FRACTION WITH GUANETHIDINE AND GUANADREL

(71) Applicant: M2SP LLC, Califon, NJ (US)

(72) Inventors: Mathew Maurer, Califon, NJ (US); Marc Grodman, Califon, NJ (US)

(73) Assignee: M2SP LLC, Califon, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/050,547

(22) Filed: Feb. 11, 2025

(65) Prior Publication Data

US 2025/0177415 A1 Jun. 5, 2025

Related U.S. Application Data (63) Continuation-in-part of application No. PCT/US2023/074483, filed on Sep. 18, 2023.

(60) Provisional application No. 63/486,280, filed on Feb. 22, 2023, provisional application No. 63/376,121, filed on Sep. 19, 2022.

(51) Int. Cl.
| | | |
|---|---|---|
| *A61K 31/34* | (2006.01) | |
| *A61K 31/36* | (2006.01) | |
| *A61K 31/395* | (2006.01) | |
| *A61K 31/554* | (2006.01) | |
| *A61K 45/06* | (2006.01) | |
| *A61P 9/04* | (2006.01) | |

(52) U.S. Cl.
CPC .......... *A61K 31/5545* (2017.08); *A61K 31/36* (2013.01); *A61K 45/06* (2013.01); *A61P 9/04* (2018.01)

(58) Field of Classification Search
CPC ............................ A61K 31/34; A61K 31/5545
USPC ................................................. 514/183, 462
See application file for complete search history.

(56) References Cited

U.S. PATENT DOCUMENTS

| | | | |
|---|---|---|---|
| 2,928,829 | A | 3/1960 | Mull |
| 11,083,877 | B2 | 8/2021 | Seward |
| 2004/0058908 | A1 | 3/2004 | Keller et al. |
| 2020/0087367 | A1 | 3/2020 | Li et al. |

OTHER PUBLICATIONS

International Search Report and written opinion issued in PCT/US2023/074483 on Dec. 19, 2023.
C. Liang, "Sympatholysis and cardiac sympathetic nerve function in the treatment of congestive heart failure", J Am Coll Cardiol, 2003, 42(3):549-551.
Woosley et al., "Drug Therapy—Guanethedine", Medical Intelligence, 1976, 295(19):1053-1057.
Chapter 16, M. Tendera et al., "Treatment of Diastolic Heart Failure", p. 223-239, in Diastolic Heart Failure, 2008, edited by O. Smiseth (Springer).
Gaffney et al., "Importance of the adrenergic nervous system in the support of circulatory function in patients with congestive heart failure", Am J Medicine, 1963, 34(3):320-324 (abstract only).
Gaffney et al., "Study of the Relationship Between the Neurotransmitter Store and Adrenergic Nerve Block Induced by Reserpine and Guanethidine", Circulation Research, 1963, vol. XII, p. 264-268.
Glaubiger et al., "Chronic guanethidine treatment increases cardiac beta-adrenergic receptors", Nature, 1978, 273:240-242.
Fudim et al., "Splanchnic Nerve Block Mediated Changes in Stressed Blood Volume in Heart Failure", JACC: Heart Failure, 2021, 9(4):293-300.
Fudim et al., "Venous Tone and Stressed Blood Volume in Heart Failure", J. Am. College of Cardiology (JACC), 2022, 78(18):1858-1869.
Braunwald et al., "The Control of Ventricular Function in Man", Brit. Heart J., 1965, 27:1-16.
Mason et al., "Effects of Guanethidine, Reserpine, and Methyldopa on Reflex Venous and Arterial Constriction in Man", J Clin Investigation, 1964, 43(7):1449-1463.
Braunwald et al., "Reflex Control of the Systemic Venous Bed: Effects on Venous Tone of Vasoactive Drugs, and of Baroreceptor and Chemoreceptor Stimulation", Circulation Research, 1963, vol. XII, p. 539-552.
Harrison et al., "Relationships Between the Release and Tissue Depletion of Norepinephrine from the Heart by Guanethidine and Reserpine", Circulation Research, 1963, vol. XII, p. 256-263.
Gaffney et al., "Effects of Reserpine and Guanethidine on Venous Reflexes", Circulation Research, 1962, vol. XI, p. 889-894.
Gaffney et al., "Analysis of the Acute Circulatory Effects of Guanethidine and Bretylium", Circulation Research, 1962, vol. X, p. 83-88.
Pfeffer et al., "Favorable effects of therapy on cardiac performance in spontaneously hypertensive rats", Am. J. Physiol., 1982, 242 (Heart Circ. Physiol. 11):H776-H784.
Ferguson, R K., et al., "Patient Acceptance of Guanethidine as Therapy for Mild to Moderate Hypertension. A Comparison with Reserpine," American Heart Association Journals, Circulation, Jul. 1976, 54(1), pp. 32-37.
Owens, S D., "Efficacy and Safety of Guanadrel in Elderly Hypertensive Patients," Archives of Internal Medicine, Jul. 1988, 148(7), pp. 1515-1518.
Pollentier, B., et al., "Examination of the Six Minute Walk Test to Determine Functional Capacity in People with Chronic Heart Failure: a Systematic Review," Cardiopulmonary Physical Therapy Journal, Mar. 2010, 21(1), pp. 13-21.
Sramko, M., "Resting and Exercise-Induced Left Atrial Hypertension in Patients With Atrial Fibrillation: The Causes and Implications for Catheter Ablation," JACC: Clinical Electrophysiology, May 2017, 3(5), pp. 461-469.

*Primary Examiner* — Raymond J Henley, III
(74) *Attorney, Agent, or Firm* — Blank Rome LLP (57) ABSTRACT

The present invention is directed to a method of treating a patient diagnosed with or suffering from heart failure with preserved ejection fraction (HFpEF) by administering an effective amount of a peripherally-acting antihypertensive agent that reduces excessive venoconstriction (such as guanethidine, guanadrel, or a pharmaceutically acceptable salt thereof), alone or in combination with other agents.

20 Claims, 3 Drawing Sheets

TREATMENT FOR HEART FAILURE WITH PRESERVED EJECTION FRACTION WITH GUANETHIDINE AND GUANADREL

This application is a continuation-in-part of International Application No. PCT/US2023/074483, filed Sep. 18, 2023, which claims the benefit of U.S. Provisional Application Nos. 63/376,121, filed Sep. 19, 2022, and 63/486,280, filed Feb. 22, 2023, each of which is hereby incorporated by reference in its entirety.

FIELD OF THE INVENTION

The present invention is directed to a method of treating a patient diagnosed with or suffering from heart failure with preserved ejection fraction (HFpEF) by administering an effective amount of guanethidine, guanadrel, or a pharmaceutically acceptable salt thereof, alone or in combination with other agents.

BACKGROUND

Despite progressive declines in age-adjusted mortality rates from coronary heart disease and hypertensive cardiovascular disease, both the incidence and prevalence of heart failure are increasing and projected to continue to rise well into the $21^{st}$ Century (Tsao et al., Heart Disease and Stroke Statistics-2022 Update: A Report From the American Heart Association, Circulation 145 (8): e153-e639, 2022). The incidence and prevalence of heart failure are strikingly age-dependent, with prevalence rates in adults over 80 years of age approaching 10% and mortality rates increasing exponentially with advancing age in all major demographic subgroups of the United States population. Although several factors have contributed to the rise in heart failure, principal among them is the progressive aging of the population. The exponential increase in the prevalence of heart failure has been attributed to the increase in prevalence and cumulative duration of systemic hypertension and coronary artery disease with advancing age and age-related changes in cardiac structure and function, which occur even in the absence of overt clinically defined cardiovascular disease (Lakatta et al., *Circulation*, 107 (1): 139-46, 2003; Lakatta et al., *Circulation*, 107 (2): 346-54). Consistent with the high prevalence and substantial mortality associated with this disorder, heart failure is currently the leading indication for a cardiovascular hospital admission in adults older than 65 years of age. It is not only the most common diagnosis related group in the Medicare population, but also among the most costly, with estimated annual inpatient expenditures in the United States in excess of $40 billion (Tsao et al. 2022).

While heart failure presently affects over 7 million Americans, more than half have have normal left ventricular systolic function commonly referred to as HFpEF (heart failure with a preserved ejection fraction). Heart failure in the United States annually results in over 280,000 deaths, over one million hospitalizations, 1.8 million office visits, and almost 700,000 emergency room visits (Benjamin et al., *Circulation*, 2018, 137: e67-e492). HF hospitalizations account for over 6.5 million hospital days and a substantial portion of the billions that is spent each year on HF in the United States (Gheorghiade et al., *J Am Coll Cardiol*, 2013, 61:391-403), which is expected to rise to $53.1 billion by 2030 (Ziaeian et al., *Nat Rev Cardiol*, 2016, 13:368-78). Worldwide there are an estimated 30 million individuals with HFpEF.

Heart failure with a preserved ejection fraction, the most common form of heart failure, is a heterogeneous clinical syndrome that has proved difficult to treat. Heart failure is defined by an inability of the heart to pump blood to the body at a rate commensurate with its needs, or to do so only at the cost of high filling pressures. HFpEF is characterized by an abnormal increase in left ventricular filling pressures at rest or with exertion, in the setting of a preservation of the ratio of stroke volume to end diastolic volume (e.g. ejection fraction).

There remains a need for more effective treatments for HFpEF.

SUMMARY OF THE INVENTION

The present invention relates to the use of peripherally-acting antihypertensive agents that reduce excessive venoconstriction in a patient to treat HFpEF. Such peripherally-acting antihypertensive agents include guanethidine, guanadrel, and pharmaceutically acceptable salts thereof. In one embodiment, these peripherally-acting antihypertensive agents include those that reduce the release of catecholamines (such as norepinephrine), deplete peripheral catecholamine, decrease peripheral vascular resistance, or any combination of any of the foregoing.

One embodiment is a method of treating a patient diagnosed with, or suffering from, HFpEF comprising administering to the patient an effective amount of guanethidine, guanadrel, or a pharmaceutically acceptable salt thereof.

Another embodiment is a method of enhancing exercise capacity, health status, or both in a patient having HFpEF comprising administering to the patient an effective amount of guanethidine, guanadrel, or a pharmaceutically acceptable salt thereof.

Yet another embodiment is a method of reducing exercise-induced increases of central venous pressure (CVP), pulmonary capillary wedge pressure (PCWP), or both in a patient comprising administering to the patient an effective amount of guanethidine, guanadrel, or a pharmaceutically acceptable salt thereof. In one embodiment, the patient has HFpEF.

Yet another embodiment is a method of improving the health related quality of life and/or the functional capacity (such as the exercise capacity) in a patient diagnosed with, or suffering from, HFpEF comprising administering to the patient an effective amount of guanethidine, guanadrel, or a pharmaceutically acceptable salt thereof. The health related quality of life may be measured by a questionnaire (such as KCCQ or KCCQ-12). In one embodiment, the health related quality of life or exercise capacity is measured by a walk test, for example a 6 minutes walk test, or by the maximum oxygen uptake.

Yet another embodiment is a method of reducing the risk of cardiovascular death, or reducing the risk of cardiovascular hospitalization in a patient diagnosed with, or suffering from, HFpEF comprising administering to the patient an effective amount of guanethidine, guanadrel, or a pharmaceutically acceptable salt thereof.

Yet another embodiment is a method of reducing the risk of the new onset of atrial fibrillation in a patient diagnosed with, or suffering from, HFpEF comprising administering to the patient an effective amount of guanethidine, guanadrel, or a pharmaceutically acceptable salt thereof.

Yet another embodiment is a method of treating a patient diagnosed with, or suffering from, HFpEF comprising administering to the patient an effective amount of (a) guanethidine, guanadrel, or a pharmaceutically acceptable salt thereof and (b) one or more second therapeutic agents selected from a diuretic (such as a thiazide diuretic or loop diuretic), angiotensin converting enzyme (ACE) inhibitor, angiotensin receptor antagonist (either alone or in combination with a neutral endopeptidase inhibitor), mineralocorticoid antagonist (MRA), calcium channel blocker, beta-blocker, neprilysin inhibitor, angiotensin receptor-neprilysin inhibitor, angiotensin II receptor blocker (ARB), aldosterone antagonist, sodium-glucose cotransporter-2 (SGLT-2) inhibitor, GLP-1 receptor agonist, gastric inhibitory polypeptide (GIP) receptor agonist, dual GLP-1/GIP receptor agonist, or any combination of any of the foregoing. In one embodiment, the second therapeutic agent is a GLP-1 receptor agonist. In another embodiment, the second therapeutic agent is a dual GLP-1/GIP receptor agonist.

Yet another embodiment is a method of improving the health related quality of life and/or the functional capacity (such as the exercise capacity) in a patient having HFpEF comprising administering to the patient an effective amount of (a) guanethidine or a pharmaceutically acceptable salt thereof and (b) one or more second therapeutic agents selected from a diuretic (such as a thiazide diuretic or loop diuretic), angiotensin converting enzyme (ACE) inhibitor, angiotensin receptor antagonist (either alone or in combination with a neutral endopeptidase inhibitor), mineralocorticoid antagonist (MRA), calcium channel blocker, beta-blocker, neprilysin inhibitor, angiotensin receptor-neprilysin inhibitor, angiotensin II receptor blocker, aldosterone antagonist, sodium-glucose cotransporter-2 (SGLT-2) inhibitor, GLP-1 receptor agonist, gastric inhibitory polypeptide (GIP) receptor agonist, dual GLP-1/GIP receptor agonist, or any combination of any of the foregoing. In one embodiment, the second therapeutic agent is a GLP-1 receptor agonist. In another embodiment, the second therapeutic agent is a dual GLP-1/GIP receptor agonist.

Yet another embodiment is a method of reducing the risk of cardiovascular death, reducing the risk of cardiovascular hospitalization, or reducing the risk of the new onset of atrial fibrillation in a patient diagnosed with, or suffering from, HFpEF comprising administering to the patient an effective amount of (a) guanethidine, guanadrel, or a pharmaceutically acceptable salt thereof and (b) one or more second therapeutic agents selected from a diuretic (such as a thiazide diuretic or loop diuretic), angiotensin converting enzyme (ACE) inhibitor, angiotensin receptor antagonist (either alone or in combination with a neutral endopeptidase inhibitor), mineralocorticoid antagonist (MRA), calcium channel blocker, beta-blocker, neprilysin inhibitor, angiotensin receptor-neprilysin inhibitor, angiotensin II receptor blocker, aldosterone antagonist, sodium-glucose cotransporter-2 (SGLT-2) inhibitor, GLP-1 receptor agonist, gastric inhibitory polypeptide (GIP) receptor agonist, dual GLP-1/GIP receptor agonist, or any combination of any of the foregoing. In one embodiment, the second therapeutic agent is a GLP-1 receptor agonist. In another embodiment, the second therapeutic agent is a dual GLP-1/GIP receptor agonist.

The exercise capacity of a patient can be assessed by measuring the maximal exercise capacity or submaximal exercise capacity (e.g., a 6-minute walk test (6MWT or 6-MWT)) of the patient. In one embodiment, the patient having HFpEF has below normal or poor maximal exercise capacity. In another embodiment, the patient having HFpEF has below normal or poor submaximal exercise capacity (for instance, as measured by 6MWT). Normal exercise capacity is that for an average healthy patient of similar age. In another embodiment, exercise capacity of a patient is assessed by measuring peak oxygen consumption. The health status of a patient can be assessed by the Kansas City Cardiomyopathy Questionnaire (KCCQ).

In one embodiment, the second therapeutic agent in the methods described herein is selected from a beta-blocker, an ACE inhibitor, angiotensin receptor blocker, diuretic, aldosterone antagonist, or any combination of any of the foregoing. In one embodiment, the second therapeutic agent is a diuretic.

In one embodiment, the patient has been diagnosed with HFpEF prior to administration of the guanethidine or a pharmaceutically acceptable salt thereof.

In another embodiment, the patient has HFpEF and an LVEF greater than 35%, 40%, 45%, 50%, or 55%. For example, the patient can have an LVEF greater than 55%. In yet another embodiment, the patient has HFpEF and an LVEF of 40 to 50% or 40 to 55%.

In yet another embodiment, the patient with HFpEF exhibits (i) a LVEF of greater than 50% and (ii) evidence of spontaneous (at rest) or provokable (e.g., during exercise or a fluid challenge) increased left ventricular filling pressures (e.g., elevated natriuretic peptide, noninvasive and/or invasive hemodynamic measurement).

In one embodiment of any of the methods described herein, the patient suffers from HFpEF and pulmonary hypertension.

Yet another embodiment is a pharmaceutical composition comprising (a) guanethidine, guanadrel, or a pharmaceutically acceptable salt thereof and (b) one or more second therapeutic agents selected from a diuretic (such as a thiazide diuretic or loop diuretic), angiotensin converting enzyme (ACE) inhibitor, angiotensin receptor antagonist (either alone or in combination with a neutral endopeptidase inhibitor), mineralocorticoid antagonist (MRA), calcium channel blocker, beta-blocker, neprilysin inhibitor, angiotensin receptor-neprilysin inhibitor, angiotensin II receptor blocker, aldosterone antagonist, sodium-glucose cotransporter-2 (SGLT-2) inhibitor, GLP-1 receptor agonist, gastric inhibitory polypeptide (GIP) receptor agonist, dual GLP-1/GIP receptor agonist, or any combination of any of the foregoing. In any of the methods described herein, the guanethidine, guanadrel or combination thereof with or without a second therapeutic agent may be administered in the form of a pharmaceutical compositions described herein. The pharmaceutical composition may be in the form of an oral dosage form and may be administered orally. In one embodiment, the second therapeutic agent is a GLP-1 receptor agonist. In another embodiment, the second therapeutic agent is a dual GLP-1/GIP receptor agonist.

DETAILED DESCRIPTION OF THE INVENTION

Subjects with HFpEF are characterized by an rise in ventricular filling pressures at rest or with exercise in order to maintain a cardiac output sufficient to meet the needs of the body. Without being bound by any particular theory, the inventors theorize that a targetable explanation for the high filling pressures is increases in stressed volume mediated by structural alterations in the veins and/or secondary to excessive venoconstriction. The excessive venoconstriction can be addressed by guanethidine or guanadrel.

It is clear that profound peripheral vascular abnormalities are an integral part of hypertension and the syndrome of heart failure. Zelis et al., *Cardiovasc Dis.* 1982, 24 (6): 437-59; Arnold et al., *Circulation.* 1991, 84 (6): 2418-25. Generalized vasoconstriction is present partly because of activation of the sympathetic nervous system and the renin angiotensin system. Francis et al., *Circulation,* 1990, 82 (5): 1724-9. Vasoconstriction has been demonstrated in both the arteries and the veins, although the major emphasis has been placed on the study of the arterial system over the past decades.

Veins serve an important, often overlooked, variable blood storage function. The large capacity of these vessels permits this low-pressure reservoir to contain more than 70% of the systemic blood volume based on data from nonhuman species. Rothe, *Physiol Rev.* 1983, 63:1281-1342. In normal subjects, more than half of the total blood volume is contained in extrathoracic veins. The capacitance of the extrathoracic veins is largely under control of the adrenergic nervous system. Aellig, *Br J Clin Pharmacol,* 1994, 38 (4): 289-305. As a result, reflex alterations in venous vasomotor tone provide a rapidly acting mechanism for compensatory redistribution of the blood volume. For example, venoconstriction acts to restore partially a normal cardiac preload during the assumption of upright posture. Additionally, Guyton (Banet and Guyton, *Am J Physiol,* 1971, 220:662-666) has shown that intact cardiovascular reflexes mediated through venous vasoconstriction prevent pooling of blood in the peripheral circulation, which is essential for the development of a full cardiac output response to increased metabolism. An increase in central blood volume from venoconstriction with a concomitant reduction in peripheral venous capacitance could result in an increased preload and provide an explanation for the higher filling pressures characteristic of heart failure in the setting of normal systolic function or heart failure with a preserved jection fraction. A theoretical analysis (Burkhoff et al., *Am J Physiol,* 1993, 265 (5 Pt. 2): H1819-28) suggests that elevations of pulmonary venous pressures that occur in the setting of acute pulmonary edema do not occur simply as a direct hemodynamic consequence of left ventricular systolic or diastolic dysfunction but rather, are dictated more by sympathetic control on venous capacity.

A majority of patients with heart failure and normal systolic function are elderly. Physiologic differences in venous capacitance, venous tone and possibly venous responses to sympathetic stimulus with age have been described and support the role of the venous system in the genesis of HFpEF. Elderly patients demonstrate a reduced limb venous compliance and capacitance compared to younger subjects. Olsen et al., *Am J Physiol.* 1998; 275 (3 Pt 2): H878-H886; Olsen et al., *Am J Physiol.* 2000; 278: H222-H232. The autonomic control of the cardiovascular system regulated by both α- and β-adrenergic receptors changes with age. While the density of β-receptors appears unaltered with age, there is a marked decrease in the response of the cardiovascular system to β-adrenergic stimulation with age. Mechanisms include down-regulation and decreased agonist binding of β 1-receptors, uncoupling of β 2-receptors, and altered signal transduction. O'Malley et al., *J Hypertension,* 1988; 6 (suppl 1): S59-S62. In contrast, a 1-receptor mediated constriction is maintained with age at least until the seventh decade. Klein et al., *Clin Pharmacol Ther.* 1990; 47:535-539. For example, the ability of phenylephrine (a 1-agonist) to raise blood pressure is unaltered by aging in human subjects. Shigemi et al., *Am J Physiol.* 1994; 267: H210-H210. The combination of decreased venodilatory β-2 and preserved constrictive α 1-receptors could produce an increase in resting venous tone. This coupled with decreased peripheral venous capacity would result in an increase in the volume in the central compartment. Increased venous tone in healthy elderly subjects has been suggested in one study. Gascho et al., *Am J Cardiol.* 1989; 63:1267-1270.

In subjects with hypertension, not reported to have heart failure, the effective compliance, a measure of effect of blood volume on the central venous pressure, was lower than among controls. Walsh et al., *Cardiovasc Res* 1969, 3:338. Since the arterial system is an insignificant contributor of effective compliance (Guyton et al., *Am J Physiol* 1959; 5:1008-1014; Echt et al., *Circ Res* 1974; 33:61), the compliance of the total circulation is mainly related to the properties of the venous side of the circulation. Thus, the decreased effective compliance in hypertensive patients suggests that venous distensibility is reduced, which likely is the result of sympathetic stimulation. In fact, the compensatory increase in preload that results from venoconstriction in essential hypertension can explain why these patients have high cardiac outputs despite very high arteriolar resistance (Liu et al., 1993, *Circulation,* 88 (4 Pt 1): 1893-906) and normalized effective arterial elastance as demonstrated in our data (Maurer et al., *J Am Coll Cardiol,* 2007 March, 49 (9): 972-81).

In summary, the venous system is not only an understudied and under appreciated regulator of cardiovascular function, but based on classic physiologic principles, it likely plays a significant mechanistic role in the development of the syndrome of heart failure with a preserved ejection fraction (HFpEF). Without being bound by any particular theory, the inventor theorizes that a decrease in peripheral venous capacitance from sympathetic stimulation results in an increased central volume and is among the major pathophysiologic mechanism underlying the morbidity associated with HFpEF.

While investigations have focused on abnormalities of the left or right ventricular structure or function as the principle cause of the high filling pressures, classic Guytonian physiology (Guyton et al., *Annu Rev Physiol.* 1972, 34:13-46; Guyton et al., *Clin Anesth.* 1964, 3:1-34) dictates that ventricular filling pressures are predominately determined by alterations in loading conditions (preload more than afterload) and less so by the cardiac chamber properties. In mammals, 70% of the blood volume is stored in the venous system (Rothe, *Physiol Rev.* 1983, 63:1281-1342) and the venous system is roughly 30 times more compliant than the arterial system (Gelman, *Anesthesiology,* 2008, 108 (4): 735-748). Simulations of the cardiovascular system (Burkhoff et al., *Am J Physiology*, 1993, 265 (5 Pt 2): H1819-28) and physiologic experiments (Tyberg, *Pflugers Arch.* 2002, 445 (1): 10-7; Tyberg et al., *Adv Exp Med Biol.* 1993, 346:313-7) demonstrate that alterations in venous capacitance by modulating the relationship between stressed and unstressed volume (Fudim et al., *J Am Coll Cardiol.* 2022, 10; 79 (18): 1858-1869) are important factors that contribute to the excessive rise in left ventricular filling pressures in patients with HFpEF with exercise or during acute decompensation. In further support of the role of venous abnormalities in the genesis of HFpEF, a disorder predominately of older adults, venous properties are markedly altered with human aging principally due to altered beta receptor density and sensitivity with marked declines in veins ability to dialate (Pan et al., *J Pharmacol Exp Ther.* 1986, 239 (3): 802-7). Thus, an important and previously overlooked mechansism in HFpEF that underlies the exercise intolerance and the development of acute pulmonary edema and less severe forms of acute decompensted heart failure leading to hospitalizations may be alterations in venous properties. Accordingly, while many mechanisms likely contribute to the limitations in exercise and the ability to perform activities of daily living in HFpEF, there is growing evidence of profoundly abnormal hemodynamic response to exercise characterized by rapid and marked elevation in right and left heart filling pressures, which typically return to baseline values during recovery (Bourlaug et al., *Circ Heart Fail.*, 2010, 3 (5): 588-595). These rapid rises in filling pressures may be mediated by shifts in blood volume from principally the splanchnic bed to the central circulation by venous constriction. While investigation using device based therapies to ablate the sympathetic control of the venous splanchnic bed are being evaluated (see, e.g., Clinicaltrials.gov identifier: NCT04592445) as a therapy for HFpEF, there is currently no approved pharamacologic therapy to address these venous abnormalities in HFpEF. Previous studies of nitrates failed to show a clinical benefits in patients with HFpEF (Redfield et al., *N Engl J Med.*, 2015, 373 (24): 2314-24). Nitrates, however, have complex effects on both venous and arterial properties and there is a potential for tachyphylaxis.

Guanethidine is a peripherally-acting antihypertensive agent that reduces the release of catecholamines, such as norepinephrine. Guanethidine is transported across the sympathetic nerve membrane by the same mechanism that transports norepinephrine itself (NET, uptake 1), and uptake is essential for the drug's action. Once guanethidine has entered the nerve, it is concentrated in transmitter vesicles, where it replaces norepinephrine. It may also inhibit the release of granules by decreasing norepinephrine. Guanthedine blocks the normal sympathetic reflexes and causes a lowering of blood pressure by decreasing venous return and cardiac output and blunting the responsiveness of the resistance and capacitance vessels to sympathetic stimuli (Woosley et al., *N Eng J Med*, 1976, 295:1053-57). Without being bound by any particular theory, the inventor hypothesizes that guanethidine by blunting the sympathetic stimulus that results in venoconstriction and drives the distribution of blood volume to the central circulation, is an effective therapy for patients with HFpEF.

Guanethidine has actions that are uniquely targeted to the peripheral sympathetic nervous system and relax the peripheral venous system. Its selective action results from the fact that the drug is a substrate for the pump that transports norepinephrine into the nerve ending. Guanethidine is actively transported into the neuron by this "norepinephrine pump"; inhibition of the norepinephrine pump also inhibits guanethidine uptake and action. Once in the adrenergic neuron, guanethidine binds to the norepinephrine storage vesicles and releases norepinephrine from the nerve ending. In addition to depletion of norepinephrine, guanethidine blocks the release of catecholamines normally produced by nerve stimulation.

Other peripherally-acting antihypertensive agents that reduce excessive venoconstriction in a patient can be used in lieu of guanethidine or guanadrel. Such agents include those that reduce the release of catecholamines (such as norepinephrine), deplete peripheral catecholamine, decrease peripheral vascular resistance, or any combination of any of the foregoing.

Unless specifically stated or obvious from context, as used herein, the term "or" is understood to be inclusive.

Unless specifically stated or obvious from context, as used herein, the terms "a", "an", and "the" are understood to be singular or plural.

Ranges provided herein are understood to be shorthand for all of the values within the range.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The terms "treat," "treatment," and "treating" in the context of the administration of a therapy to a patient refers to the reduction or inhibition of the progression and/or duration of a disease or condition, the reduction or amelioration of the severity of a disease or condition, and/or the amelioration of one or more symptoms thereof resulting from the administration of one or more therapies.

The term "administering" includes, but is not limited to, oral administration, administration as a suppository, topical contact, intravenous, transdermal, parenteral, intraperitoneal, intramuscular, intralesional, intrathecal, intranasal, rectal, percutaneous, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. In embodiments, the administering does not include administration of any active agent other than the recited active agent. One preferred route of administration is the oral route.

The term "combination" refers to an assemblage of reagents (e.g., active ingredients or drugs) for use in therapy either by simultaneous, contemporaneous, or fixed-dose combination delivery. Simultaneous delivery refers to delivery of an admixture (whether a true mixture, a suspension, an emulsion or other physical combination) of the drugs. In this case, the combination may be the admixture or separate containers of the guanethidine (or its pharmaceutically acceptable salt) and a second agent that are combined just prior to delivery. Contemporaneous delivery refers to the separate delivery of the guanethidine (or its pharmaceutically acceptable salt) and second agent at the same time, or at times sufficiently close together that an additive or preferably synergistic activity relative to the activity of either the guanethidine (or its pharmaceutically acceptable salt) or the cardiovascular drug alone is observed. Fixed-dose combination delivery refers to the delivery of two or more drugs contained in a single dosage form for oral administration, such as a capsule or tablet.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, delay, inhibition, suppression, or reduction of a symptom or symptoms of a disease or disorder, which could also be referred to as a "therapeutically effective amount." A "reduction" of a symptom or symptoms (and grammatical equivalents of this phrase) means decreasing of the severity or frequency of the symptom(s), or elimination of the symptom(s). An "effective amount" of a drug can be an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage *Calculations* (1999); and *Remington: The Science and Practice of Pharmacy*, 20th Edition, 2003, Gennaro, Ed., Lippincott, Williams & Wilkins). Dosages may be varied depending upon the requirements of the patient and the compound being employed. The dose administered to a patient, in the context of the present disclosure, should be sufficient to effect a beneficial therapeutic response in the patient over time. The size of the dose may also be determined by the existence, nature, and extent of any adverse side-effects. Determination of the proper dosage for a particular situation is within the skill of the practitioner.

As used herein, the terms "subject" and "patient" are used interchangeably and refer to a human or mammal patient unless indicated otherwise. Suitable mammals include, but are not limited to, domestic animals (such as cats and dogs), horses, sheep, goats, and pigs. In a preferred embodiment, the patient is a human patient. In one embodiment, the patient is at least 40 years of age. In another embodiment, the patient is at least 50 years of age. Inyet another embodiment, the patient is at least 60 or 65 years of age.

"HFpEF" or "heart failure with preserved ejection fraction (also known as diastolic heart failure) is typically diagnosed upon recognition of heart failure and preserved ejection fraction. Ejection fraction can be assessed by two-dimensional transthoracic echocardiography (TTE). HFpEF may be diagnosed based on 2022 AHA/ACC/HFSA Guideline for the Management of Heart Failure (*Circulation*, 2022, 145 (18): e895-e1032) (see section 2.2 and 2.3), which is hereby incorporated by reference in its entirety. Common symptoms of HFpEF include, but are not limited to, fatigue, weakness, dyspnea, orthopnea, paroxysmal nocturnal dyspnea, and edema. HFpEF may be characterized by a decrease in left ventricular compliance, or as we hypothesize alterations in loading conditions leading to increased pressure in the left ventricle. Increased left atrial size is often seen with HFpEF as a result of the chronically or intermittently high left ventricular end diastolic pressures and hence high left atrial pressure. HFpEF corresponds to diagnosis code 150.3 in the 2022 ICD-10-CM (ICD-10 Clinical Modification).

In one embodiment, the patient with HFpEF exhibits a LVEF of greater than 35%. In another embodiment, the patient with HFpEF exhibits a LVEF of greater than 40%. In another embodiment, the patient with HFpEF exhibits a LVEF of greater than 45%. In yet another embodiment, the patient with HFpEF exhibits a LVEF of greater than 50%. In yet another embodiment, the patient with HFpEF exhibits a LVEF of 36% to 50%, or 41% to 50%.

In another embodiment, the patient with HFpEF exhibits (i) a LVEF of greater than 50% and (ii) evidence of spontaneous (at rest) or provokable (e.g., during exercise or a fluid challenge) increased left ventricular filling pressures (e.g., elevated natriuretic peptide, noninvasive and/or invasive hemodynamic measurement).

In one embodiment, the patient has HFpEF and exercise induced left atrial hypertension (EILAH). In one embodiment, EILAH is defined as having a pulmonary capillary wedge pressure (PCWP) of no more than 15 mm Hg at rest measured supine but having an exercise induced PCWP of at least 25 mm Hg. In another embodiment, the patient has been diagnosed with HFpEF and EILAH.

In another embodiment, the patient with HFpEF exhibits (i) chronic heart failure, (ii) a PCWP of no more than 15 mm Hg at rest measured supine but having an exercise induced PCWP of at least 25 mm Hg, or (iii) both. Chronic heart failure can be defined as (a) symptoms of heart failure requiring treatment (intermittent or continuous) with diuretics for at least 30 days, (b) New York Heart Association (NYHA) class II with a history of at least NYHA class II for the past year, NYHA class III, or ambulatory NYHA class IV symptoms (e.g., paroxysmal nocturnal dyspnea, orthopnea, or dyspnea on mild or moderate exertion) or signs of heart failure (e.g., any rales post cough, or chest x-ray demonstrating pulmonary congestion), and (c) at least one of the following (i) at least one heart failure (HF) hospital admission (with heart failure as the primary, or secondary diagnosis) within the 12 months of treatment initiation), (ii) treatment with intravenous (IV) diuretics, or intensification of oral diuresis for heart failure within the 12 months of treatment initiation, (iii) an N-terimal pro B-type natriuretic peptide (NT-proBNP) value greater than 150 pg/ml in normal sinus rhythm and/or greater than 450 pg/ml in atrial fibrillation within the past 6 months, or (iv) B-type natriuretic peptide (BNP) value greater 50 pg/ml in normal sinus rhythm and/or greater 150 pg/ml in atrial fibrillation within the past 6 months. In one embodiment, the HFpEF patient has chronic heart failure according to NYHA class II, III, or IV. In another embodiment, the HFpEF patient has chronic heart failure according to NYHA class I.

In one embodiment of any of the methods described herein, the patient suffers from HFpEF and pulmonary hypertension.

In HFpEF patients, there is an increased risk for congestive heart failure, atrial fibrillation, and pulmonary hypertension. Risk factors are hypertension, hyperlipidemia, diabetes, obesity, smoking, and obstructive sleep apnea. In this type of heart failure, the heart muscle contracts well but the ventricle does not fill with blood well in the relaxation phase.

Guanethidine

Guanethidine has the chemical name guanidine, [2-(hexahydro-1 (2H)-azocinyl)ethyl]-, and can be in its sulfate form, guanethidine sulfate or guanethidine monosulfate (CAS 645-43-2) with chemical name guanidine, [2-(hexahydro-1 (2H)-azocinyl)ethyl]-, sulfate (1:1). Guanethidine has been marketed under the trade name Ismelin (U.S. Food and Drug Administration New Drug Application No. 012329). Pharmaceutically acceptable salts of guanethidine include, but are not limited to, guanethidine sulfate.

The guanethidine or a pharmaceutically acceptable salt thereof may be administered in the form of a dosage form containing one or more pharmaceutically acceptable excipients, such as an oral dosage form (e.g., a tablet, capsule, granules, or oral liquid). The guanethidine or a pharmaceutically acceptable salt thereof may be administered once daily, twice daily, or more frequently. In one preferred embodiment, the guanethidine or a pharmaceutically acceptable salt thereof is administered once daily, such as in an immediate release or extended release oral dosage form. Preferably, the guanethidine or a pharmaceutically acceptable salt thereof is administered orally. In one embodiment, the guanethidine or a pharmaceutically acceptable salt thereof is administered in the form of an oral dosage form (such as a tablet or capsule) containing about 2, 3, 4, 5, 6, 7, 8, 9, 10, 15, 20, or 25 mg of guanethidine or a pharmaceutically acceptable salt thereof (based on guanethidine free base). In another embodiment, the guanethidine or a pharmaceutically acceptable salt thereof is administered in the form of an oral dosage form (such as a tablet or capsule) containing about 2 mg of guanethidine or a pharmaceutically acceptable salt thereof (based on guanethidine free base). In yet another embodiment, the guanethidine or a pharmaceutically acceptable salt thereof is administered in the form of an oral dosage form (such as a tablet or capsule) containing about 5 mg of guanethidine or a pharmaceutically acceptable salt thereof (based on guanethidine free base). In yet another embodiment, the guanethidine or a pharmaceutically acceptable salt thereof is administered in the form of an oral dosage form (such as a tablet or capsule) containing about 10 mg of guanethidine or a pharmaceutically acceptable salt thereof (based on guanethidine free base). In yet another embodiment, the guanethidine or a pharmaceutically acceptable salt thereof is administered in the form of an oral dosage form (such as a tablet or capsule) containing about 15 mg of guanethidine or a pharmaceutically acceptable salt thereof (based on guanethidine free base). In yet another embodiment, the guanethidine or a pharmaceutically acceptable salt thereof is administered in the form of an oral dosage form (such as a tablet or capsule) containing about 20 mg of guanethidine or a pharmaceutically acceptable salt thereof (based on guanethidine free base). In yet another embodiment, the guanethidine or a pharmaceutically acceptable salt thereof is administered in the form of an oral dosage form (such as a tablet or capsule) containing about 25 mg of guanethidine or a pharmaceutically acceptable salt thereof (based on guanethidine free base).

The total daily dosage of guanethidine or a pharmaceutically acceptable salt thereof (e.g., by oral administration) may range from about 0.5 or 1 to about 100 mg (based on guanethidine free base) and preferably from about 0.5, 2, or 5 to about 25 mg. In one embodiment, about 2 to about 10 mg of guanethidine or a pharmaceutically acceptable salt thereof (based on guanethidine free base) is administered orally daily. In another embodiment, about 5 to about 10 mg of guanethidine or a pharmaceutically acceptable salt thereof (based on guanethidine free base) is administered orally daily. In yet another embodiment, about 1, 2, 3, 4, 5, 7.5, or 10 mg of guanethidine or a pharmaceutically acceptable salt thereof (based on guanethidine free base) is administered daily. In another embodiment, about 5, 6, 7, 8, 9, 10, 11, 12, 13, 14, 15, 16, 17, 18, 19, or 20 mg of guanethidine or a pharmaceutically acceptable salt thereof (based on guanethidine free base) is administered daily. In yet another embodiment, about 0.5, 1, 2.5, 5, 10, or 25 mg of guanethidine or a pharmaceutically acceptable salt thereof (based on guanethidine free base) is administered daily. In another embodiment, about 1 to about 3 mg (for example, 1, 2, or 3 mg) of guanethidine or a pharmaceutically acceptable salt thereof (based on guanethidine free base) is administered daily. For example, the total daily dosage of guanethidine or a pharmaceutically acceptable salt thereof may be about 10 mg (based on guanethidine free base). In another embodiment, the total daily dosage of guanethidine or a pharmaceutically acceptable salt thereof is about 5 mg (based on guanethidine free base). In one embodiment, about 5 mg of guanethidine or a pharmaceutically acceptable salt thereof (based on guanethidine free base) is administered orally daily. In one embodiment, about 10 mg of guanethidine or a pharmaceutically acceptable salt thereof (based on guanethidine free base) is administered orally daily. In another embodiment, about 15 mg of guanethidine or a pharmaceutically acceptable salt thereof (based on guanethidine free base) is administered orally daily. In yet another embodiment, about 20 mg of guanethidine or a pharmaceutically acceptable salt thereof (based on guanethidine free base) is administered orally daily. In yet another embodiment, about 25 mg of guanethidine or a pharmaceutically acceptable salt thereof (based on guanethidine free base) is administered orally daily. Also, in a preferred embodiment, the guanethidine or a pharmaceutically acceptable salt thereof is administered once daily.

In one embodiment, the patient is orally administered 10 mg of guanethidine once daily.

Treatment with guanethidine can be initiated without a loading dose.

Guanadrel

Guanadrel has the chemical name guanidine, 2-(1,4-dioxaspiro[4.5]decan-2-ylmethyl) guanidine, and can be in its sulfate form, guanadrel with the chemical name 2-(1,4-dioxaspiro[4.5]decan-3-ylmethyl) guanidine, sulfuric acid. Guanadrel has been marketed under the trade name Hylorel (U.S. Food and Drug Administration New Drug Application No. 018104). Pharmaceutically acceptable salts of guanadrel include, but are not limited to, guanadrel sulfate. Guanadrel and its pharmaceutically acceptable salts can be prepared as described in U.S. Pat. No. 3,547,951.

The guanadrel or a pharmaceutically acceptable salt thereof may be administered in the form of a dosage form containing one or more pharmaceutically acceptable excipients, such as an oral dosage form (e.g., a tablet, capsule, granules, or oral liquid). The guanadrel or a pharmaceutically acceptable salt thereof may be administered once daily, twice daily, or more frequently. In a preferred embodiment, the guanadrel or a pharmaceutically acceptable salt thereof is administered once daily, such as in an immediate release dosage form. Preferably, the guanadrel or a pharmaceutically acceptable salt thereof is administered orally.

The total daily dosage of guanadrel or a pharmaceutically acceptable salt thereof may range from about 1 to about 100 mg (based on guanadrel free base) and preferably from about 10 to about 75 mg or from about 20 to about 75 mg. Preferably, the guanadrel or a pharmaceutically acceptable salt thereof is orally administered once daily.

Treatment with guanadrel can be initiated without a loading dose.

Other Agents

Patients can be treated with the combination (e.g., a fixed-dose combination) of guanethidine or guanadrel (or its pharmaceutically acceptable salt) and another cardiovascular agent. Suitable cardiovascular agents which can be administered with the guanethidine (or its pharmaceutically acceptable salt) include, but are not limited to, diuretics (such as a thiazide diuretic, loop diuretic, or potassium-sparing diuretic), angiotensin converting enzyme (ACE) inhibitors, angiotensin receptor antagonist (either alone or in combination with a neutral endopeptidase inhibitor), mineralocorticoid antagonist (MRA), calcium channel blockers, beta-blockers (β-adrenergic receptors blockers), neprilysin inhibitors, angiotensin receptor-neprilysin inhibitor (ARNIs) (e.g., a combination of sacubitril and valsartan such as Entresto®), angiotensin II receptor blockers (ARBs), aldosterone antagonists, sodium-glucose cotransporter-2 (SGLT-2) inhibitors, GLP-1 receptor agonists, gastric inhibitory polypeptide (GIP) receptor agonists, dual GLP-1/GIP receptor agonists, and any combination of any of the foregoing. In one preferred embodiment, the cardiovascular agent is selected from beta-blockers, ACE inhibitors, ARBs, diuretics, aldosterone antagonists, and any combination of any of the foregoing.

Suitable thiazide diuretics for use in the methods and compositions described herein include chlorothiazide, hydrochlorothiazide, chlorthalidone, indapamide, and metolazone.

Suitable loop diuretics for use in the methods and compositions described herein include furosemide, torsemide, bumetanide, and ethacrynic acid.

Suitable loop diuretics for use in the methods and compositions described herein include spironolactone and eplerenone.

Suitable ACE inhibitors for use in the methods and compositions described herein include benazepril, captopril, enalapril, fosinopril, lisinopril, moexipril, perindopril, quinapril, ramipril and trandolapril.

Suitable MRAs for use in the methods and compositions described herein include spironolactone and eplerenone.

Suitable calcium channel blockers for use in the methods and compositions described herein include amlodipine, aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nimodipine, nisoldipine, nitrendipine, and pranidipine.

Suitable beta-blockers for use in the methods and compositions described herein include epinephrine, cebutolol, atenolol, betaxolol, bisoprolol, carteolol, carvedilol, esmolol, labetalol, metoprolol, nadolol, oxprenolol, penbutolol, pindolol, propranolol, sotalol and timolol.

Suitable neprilysin inhibitors for use in the methods and compositions described herein include thiorphan, candoxatril, and candoxatrilat.

Suitable ARNIs for use in the methods and compositions described herein include a combination of sacubitril and valsartan such as Entresto®.

Suitable angiotensin II receptor blockers (ARBs) for use in the methods and compositions described herein include eprosartan, olmesartan, valsartan, telmisartan, losartan, azilsartan medoxomil, candesartan, and irbesartan.

Suitable sodium-glucose cotransporter-2 (SGLT-2) inhibitors for use in the methods and compositions described herein include atigliflozin, bexagliflozin, canagliflozin, dapagliflozin, empagliflozin, ertugliflozin, henagliflozin, ipragliflozin, luseogliflozin, remogliflozin, sotagliflozin, and tofogliflozin.

Suitable GLP-1 receptor agonists for use in the methods and compositions described herein include semaglutide, albiglutide, liraglutide, dulaglutide, lixisenatide, efpeglenatide, and exenatide.

Suitable dual GLP-1/GIP receptor agonists for use in the methods and compositions described herein include tirzepatide.

In one embodiment, the patient is treated with a combination (e.g., a fixed-dose combination) of guanethidine or guanadrel (or its pharmaceutically acceptable salt) with one or more of a diuretic, MRA, ACE inhibitor, ARB, ARNI, SGLT-2 inhibitor, GLP-1 receptor agonist, gastric inhibitory polypeptide (GIP) receptor agonist, and dual GLP-1/GIP receptor agonist.

The recommended starting dose and schedule for Entresto® is 49/51 mg orally twice daily (49 mg of sacubitril and 51 mg of valsartan). The dose is doubled after two to four weeks to the target maintenance dose of 97/103 mg twice daily. A sacubitril/valsartan composition is described in U.S. Pat. Nos. 7,468,390; 8,101,659; 8,404,744; 8,796,331; 8,877,938; and 9,388,134, the entire contents of which are incorporated by reference. Preferably, sacubitril/valsartan are administered with an ARB.

The recommended dose and schedule for hydralazine is 10 mg orally 4 times a day for the first 2 to 4 days, increased to 25 mg orally 4 times a day for the balance of the first week. This dose is increased to 50 mg orally 4 times a day for week 2 and subsequent weeks. A hydralazine composition recited hereinabove is described in U.S. Pat. Nos. 6,465,463 and 6,784,177, the entire contents of which are incorporated by reference.

Each drug can be administered in the dose and regimen as described above.

Pharmaceutical Compositions

Yet another embodiment is a pharmaceutical composition comprising (a) guanethidine, guanadrel, or a pharmaceutically acceptable salt thereof and (b) one or more second therapeutic agents selected from a diuretic (such as a thiazide diuretic or loop diuretic), angiotensin converting enzyme (ACE) inhibitor, angiotensin receptor antagonist (either alone or in combination with a neutral endopeptidase inhibitor), mineralocorticoid antagonist (MRA), calcium channel blocker, beta-blocker, neprilysin inhibitor, angiotensin receptor-neprilysin inhibitor, angiotensin II receptor blocker, aldosterone antagonist, sodium-glucose cotransporter-2 (SGLT-2) inhibitor, GLP-1 receptor agonist, gastric inhibitory polypeptide (GIP) receptor agonist, dual GLP-1/GIP receptor agonist, or any combination of any of the foregoing.

One embodiment is a pharmaceutical composition comprising (a) guanethidine or a pharmaceutically acceptable salt thereof and (b) one or more second therapeutic agents selected from a diuretic (such as a thiazide diuretic or loop diuretic), angiotensin converting enzyme (ACE) inhibitor, angiotensin receptor antagonist (either alone or in combination with a neutral endopeptidase inhibitor), mineralocorticoid antagonist (MRA), calcium channel blocker, beta-blocker, neprilysin inhibitor, angiotensin receptor-neprilysin inhibitor, angiotensin II receptor blocker, aldosterone antagonist, sodium-glucose cotransporter-2 (SGLT-2) inhibitor, GLP-1 receptor agonist, gastric inhibitory polypeptide (GIP) receptor agonist, dual GLP-1/GIP receptor agonist, or any combination of any of the foregoing. For instance, the second therapeutic agent may be a diuretic, MRA, ACE inhibitor, ARB, ARNI, SGLT-2 inhibitor, GLP-1 receptor agonist, gastric inhibitory polypeptide (GIP) receptor agonist, dual GLP-1/GIP receptor agonist, or any combination of any of the foregoing.

The pharmaceutical composition may be an oral dosage form, such as a tablet or solution. The pharmaceutical composition may be administered pursuant to the methods described herein.

The following examples are presented in order to more fully illustrate some embodiments of the invention. They should, in no way be construed, however, as limiting the broad scope of the invention.

EXAMPLES

Example 1

Figure 1:
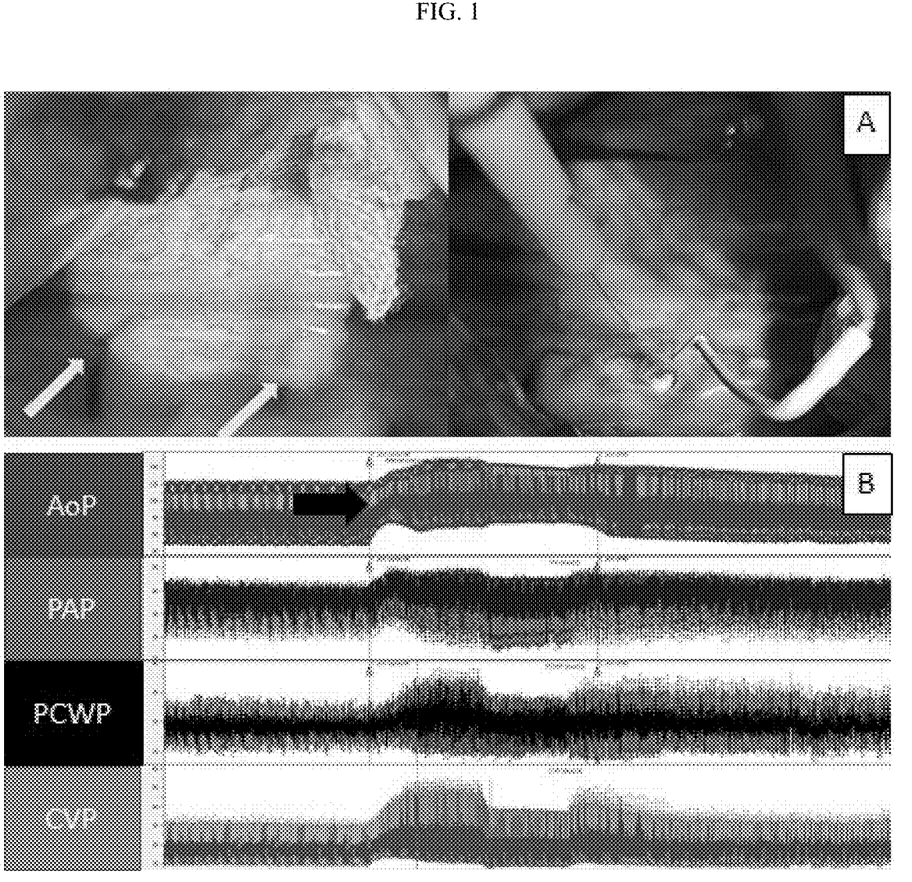
FIG. 1A are photographs showing the location of the stimulated part of the sympathetic thoracic trunk near the greater splanchnic nerve (left, yellow arrows) and electrodes in place (right), as discussed in Example 1.
FIG. 1B are graphs showing tracings of blood pressures during stimulation, as discussed in Example 1, from the top: mean aortic pressure (AoP), pulmonary artery systolic pressure (PAP), pulmonary capillary wedge pressure (PCWP) and central venous pressure (CVP). The black arrow indicates the start of the stimulation.

Experiments were conducted in anesthetized swine that underwent thoracotomy to access the left sympathetic trunk (see FIG. 1A, yellow arrows). Volume overload was achieved by IV infusion of colloid fluid and bilateral renal artery balloon-occlusion to amplify the effects of volume overload, simulating a volume overload state typical of what is observed in heart failure with a preserved ejection fraction (HFpEF). 3 minutes bursts of electric stimulation (20V, 2 ms, 20 Hz) were then applied to the sympathetic trunk near the greater splanchnic nerve (GSN), at the end of which hemodynamic data were collected while temporarily pausing mechanical ventilation.

GSN stimulations lead to an increase of mean aortic pressure (AoP) from 76.8±5.6 mm Hg to 104.4±12.5 mm Hg, pulmonary artery systolic pressure (PAP) from 37.3±4.2 mm Hg to 45.4±3.5 mm Hg, central venous pressure (CVP) from 15.7±2.7 mmHg to 18.8±2.2 mm Hg and pulmonary capillary wedge pressure (PCWP) from 18.7±1.7 mm Hg to 24.0±2.9 mm Hg (see FIG. 1B, black arrow signifies the start of stimulation).

Figure 2:
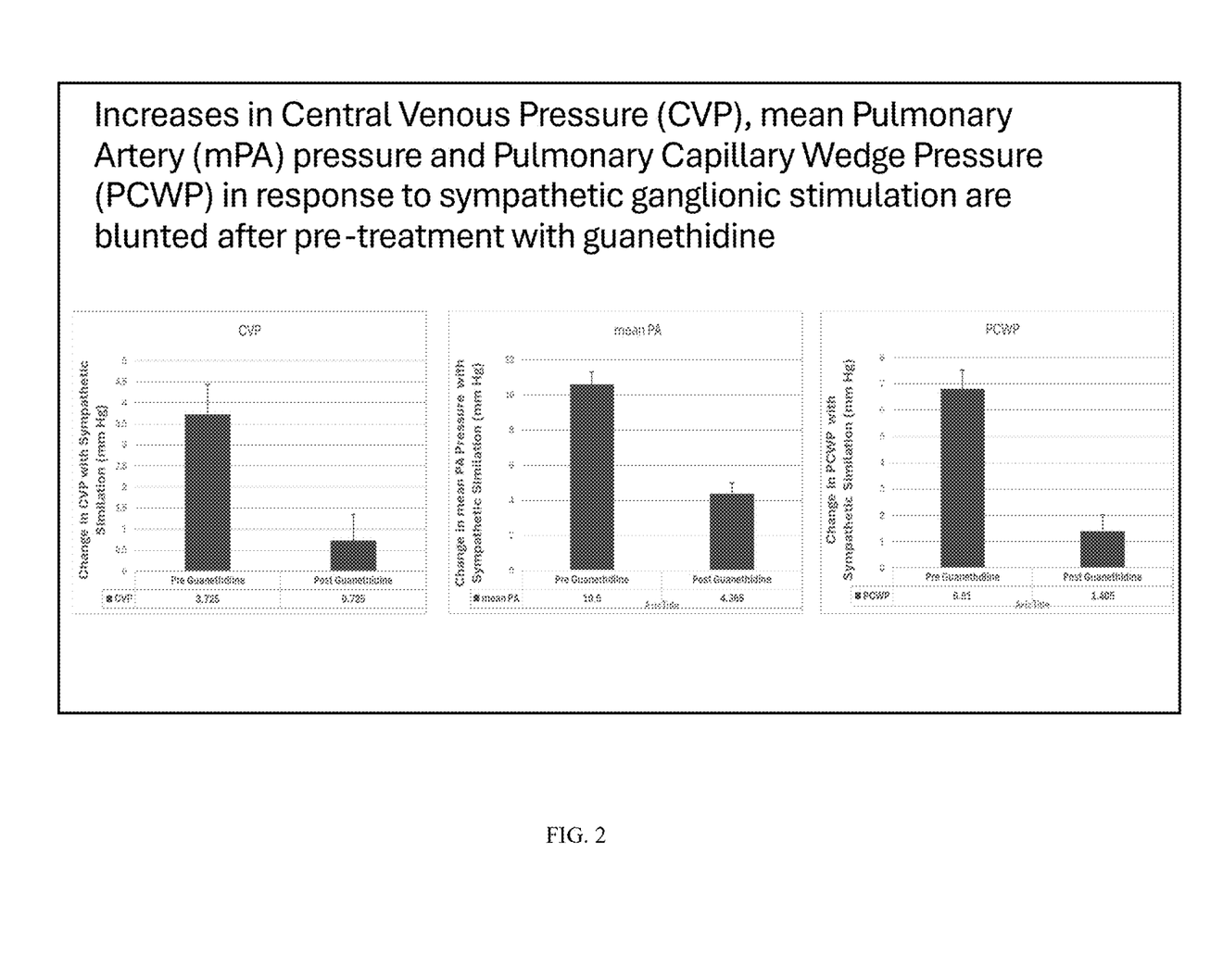
FIG. 2 are bar graphs showing the effect of sympathetic trunk stimulation in volume loaded healthy swine before and after treatment with guanethidine on the CVP, mean pulmonary artery (mPA) pressure, and PCWP, as described in Example 1.

Leveraging this model with sympathetic trunk stimulation in volume loaded healthy swine that caused increases in cardiac filling pressures that mimic hemodynamic features of HFpEF during exercise or other stresses, the effect of intravenously administered guanethidine was tested. Guanethidine was administered intravenously at a dose of 5 mg per kg (600 mg here). Once reaching steady state conditions following guanethidine infusion, CVP, mean PAP and PCWP decreased from 13.2 to 8.7 mm Hg, 31.1 to 30.7 mm Hg and 21.5 to 12.6 mm Hg, respectively. This signifies that blunting of resting sympathetic tone reduced these pressures, presumably due to vasodilation. Sympathetic trunk stimulation was performed once again and hemodynamic effects compared between pre- and post-guanethadine infusion. As shown in FIG. 2, guanethidine blunted the increase in central venous pressure (CVP), mean pulmonary artery pressures (mPA) and pulmonary capillary wedge pressure (PCWP) observed with stimulation. This data strongly supports the underlying hypothesis that increases to central pressures in HFpEF patients in response to sympathetic stimulation can be abolished by pre-treatment with guanethidine.

Figure 3:
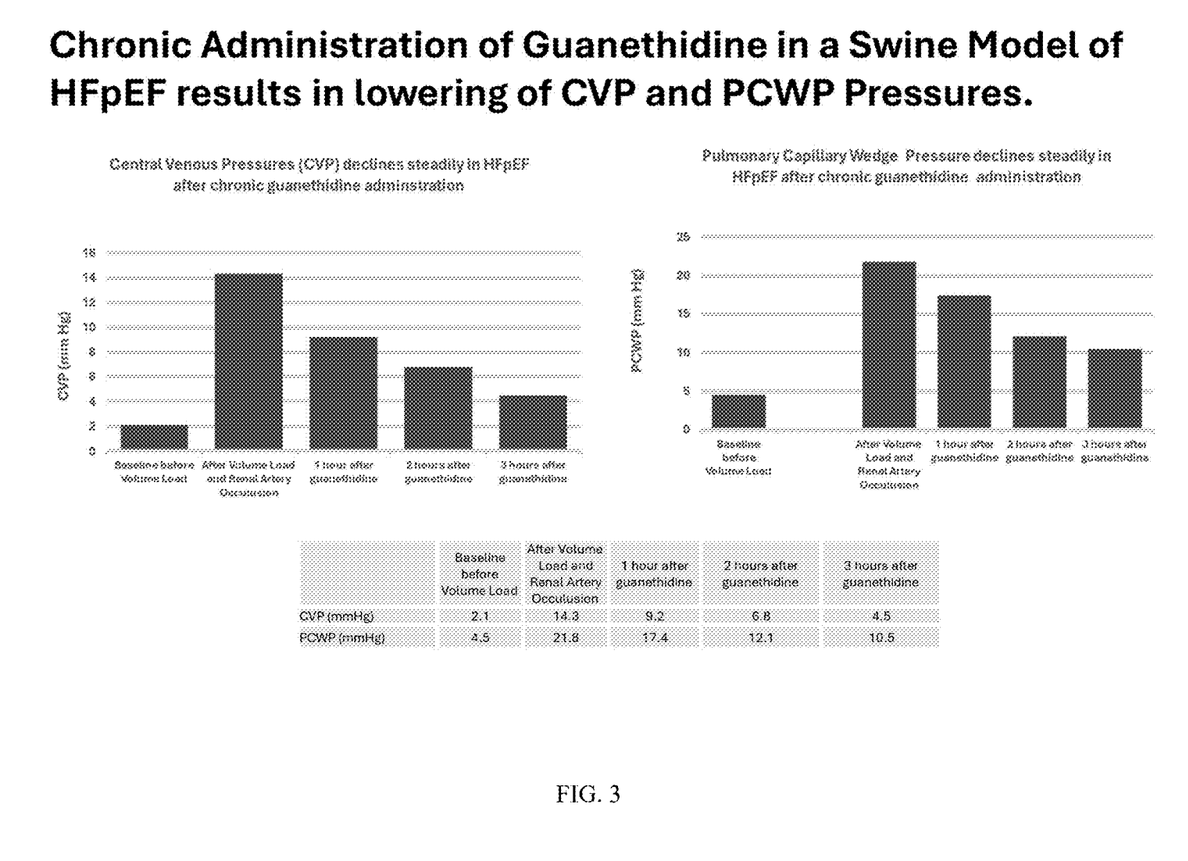
FIG. 3 are bar graphs showing CVP and PCWP at baseline before volume load, after volume load renal artery occlusion, and 1, 2, and 3 hours after guanethidine, as described in Example 1.

Additional data in an anesthetized swine model of HFpEF created by intravenous infusion of colloid fluid and bilateral renal artery balloon-occlusion to mimic the volume overload state typical of what is observed in HFpEF, demonstrated that with chronic administration of guanethidine at 5 mg/kg the central venous pressure (CVP) and pulmonary capillary wedge pressures (PCWP) declines significantly over time (see FIG. 3). These data further support the hypothesis that chronic administration of guanethidine can reduce cardiac filling pressures which are central to the pathophysiologic of heart failure with a preserved ejection fraction.

Example 2

A clinical trial evaluating the safety and efficacy of guanethidine or guanandrel would enroll patients with HFpEF and a reduced exercise capacity as evidenced by either treadmill testing, cardio-pulmonary exercise testing or submaximal testing with six minute hall walk duration or those that have a reduced health status. A more careful phenotyping of subjects could involve exercise hemodynamic studies demonstrating a marked rise in pulmonary capillary wedge pressure with exertion. Such subjects could then be randomly allocated the active agent (e.g. guanethidine (e.g., guanethidine sulfate) or guanadrel (e.g., guanadrel sulfate)) or matching placebo. Repeat testing after several weeks of therapy could assess the effect of guanethidine or guanadrel on central hemodynamics, maximal or submaximal exercise capacity or health status.

All cited patent literature and non-patent literature herein are incorporated by reference in their entireties.

The invention claimed is:

1. A method of treating a patient diagnosed with heart failure with preserved ejection fraction (HFpEF) comprising administering to the patient an effective amount of guanethidine, guanadrel, or a pharmaceutically acceptable salt thereof.

2. A method of diagnosing and treating a patient with heart failure with preserved ejection fraction (HFpEF) comprising:
    (a) diagnosing a patient as having HFpEF; and
    (b) upon a diagnosis of HFpEF, administering to the patient an effective amount of guanethidine, guanadrel, or a pharmaceutically acceptable salt thereof.

3. A method of treating a patient diagnosed with heart failure with preserved ejection fraction (HFpEF) comprising administering to the patient an effective amount of (a) guanethidine, guanadrel, or a pharmaceutically acceptable salt thereof and (b) one or more second therapeutic agents selected from a diuretic, angiotensin converting enzyme (ACE) inhibitor, angiotensin receptor antagonist, mineralocorticoid antagonist (MRA), calcium channel blocker, beta-blocker, neprilysin inhibitor, angiotensin receptor-neprilysin inhibitor, angiotensin II receptor blocker, aldosterone antagonist, sodium-glucose cotransporter-2 (SGLT-2) inhibitor, GLP-1 receptor agonist, gastric inhibitory polypeptide (GIP) receptor agonist, dual GLP-1/GIP receptor agonist, or any combination of any of the foregoing.

4. The method of claim 3, wherein the second therapeutic agent is selected from a beta-blocker, an ACE inhibitor, angiotensin receptor blocker, diuretic, aldosterone antagonist, SGLT-2 inhibitor, GLP-1 receptor agonist, gastric inhibitory polypeptide (GIP) receptor agonist, dual GLP-1/GIP receptor agonist, or any combination of any of the foregoing.

5. The method of claim 1, wherein the patient has an LVEF greater than 35%.

6. The method of claim 1, wherein the patient has an LVEF greater than 40%.

7. The method of claim 1, wherein the patient has an LVEF greater than 45%.

8. A method of treating a patient diagnosed with heart failure with preserved ejection fraction (HFpEF) comprising administering to the patient an effective amount of quanethidine, guanadrel, or a pharmaceutically acceptable salt thereof, wherein the patient has been diagnosed with HFpEF and exercise induced left atrial hypertension.

9. The method of claim 1, wherein the method comprises orally administering from about 5 to about 25 mg of guanethidine or a pharmaceutically acceptable salt thereof (based on guanethidine free base) daily.

10. The method of claim 9, wherein the method comprises orally administering about 5 mg of guanethidine or a pharmaceutically acceptable salt thereof (based on guanethidine free base) daily.

11. The method of claim 10, wherein the method comprises orally administering about 10 mg of guanethidine or a pharmaceutically acceptable salt thereof (based on guanethidine free base) daily.

12. The method of claim 11, wherein the method comprises orally administering about 15 mg of guanethidine or a pharmaceutically acceptable salt thereof (based on guanethidine free base) daily.

13. The method of claim 1, wherein the method comprises orally administering about 20 mg of guanethidine or a pharmaceutically acceptable salt thereof (based on guanethidine free base).

14. The method of claim 1, wherein the method comprises orally administering about 25 mg of guanethidine or a pharmaceutically acceptable salt thereof (based on guanethidine free base).

15. The method of claim 1, wherein the method comprises administering guanethidine free base.

16. The method of claim 1, wherein the method comprises administering guanethidine sulfate.

17. The method of claim 1, wherein the method comprises orally administering guanadrel or a pharmaceutically acceptable salt thereof.

18. The method of claim 1, wherein the method comprises administering guanadrel sulfate.

19. A method of treating a patient diagnosed with heart failure with preserved ejection fraction (HFpEF) comprising:

(a) diagnosing a patient as having HFpEF; and (b) upon a diagnosis of HFpEF, administering to the patient an effective amount of a peripherally-acting antihypertensive agent that reduces excessive venoconstriction in the patient.

20. The method of claim 19, wherein the peripherally-acting antihypertensive agent reduces the release of catecholamines, depletes peripheral catecholamine, decreases vascular resistance, or any combination of any of the foregoing.

* * * * *